United States Patent
Vaiana et al.

(10) Patent No.: US 9,234,859 B2
(45) Date of Patent: Jan. 12, 2016

(54) INTEGRATED DEVICE OF A CAPACITIVE TYPE FOR DETECTING HUMIDITY, IN PARTICULAR MANUFACTURED USING A CMOS TECHNOLOGY

(71) Applicants: STMicroelectronics S.r.l., Agrate Brianza (IT); STMicroelectronics (Crolles 2) SAS, Crolles (FR)

(72) Inventors: Michele Vaiana, Paterno' (IT); Daniele Casella, Francofonte (IT); Giuseppe Bruno, Paterno' (IT); Rosario Cariola, Giarre (IT); Benoit Gautheron, Grenoble (FR)

(73) Assignees: STMicroelectronics S.r.l., Agrate Brianza (IT); STMicroelectronics (Crolles 2) SAS, Crolles (FR)

( * ) Notice: Subject to any disclaimer, the term of this patent is extended or adjusted under 35 U.S.C. 154(b) by 0 days.

(21) Appl. No.: 14/226,554

(22) Filed: Mar. 26, 2014

(65) Prior Publication Data
US 2014/0291778 A1    Oct. 2, 2014

(30) Foreign Application Priority Data

Mar. 28, 2013   (IT) .............. TO2013A0257

(51) Int. Cl.
*H01L 29/02* (2006.01)
*G01N 27/12* (2006.01)
*G01N 27/22* (2006.01)
*H01L 49/02* (2006.01)

(52) U.S. Cl.
CPC .............. *G01N 27/225* (2013.01); *H01L 28/40* (2013.01)

(58) Field of Classification Search
CPC . H01L 28/40; H01L 2924/1305; H01L 23/34; H01L 23/5223; H01L 27/105; H01L 27/15; G01N 27/225; G01N 27/121; G01N 27/223
See application file for complete search history.

(56) References Cited

U.S. PATENT DOCUMENTS

| 4,578,693 | A | * | 3/1986 | Yazawa et al. ................ 257/444 |
| 4,612,599 | A | * | 9/1986 | Ziegler ....................... 361/283.1 |
| 6,249,130 | B1 | | 6/2001 | Greer |
| 2003/0010119 | A1 | * | 1/2003 | Toyoda ....................... 73/335.04 |

(Continued)

FOREIGN PATENT DOCUMENTS

| WO | 98/30922 A1 | 7/1998 |
| WO | 01/81931 A1 | 11/2001 |
| WO | 2007/036922 A1 | 4/2007 |

OTHER PUBLICATIONS

H. Shimizu, H. Matsumotu et al: "A Digital Hygrometer" IEEE Transactions on Instrumentation and Measurement, vol. 37, No. 2, Jun. 1988.

*Primary Examiner* — Jarrett Stark
*Assistant Examiner* — Bitew Dinke
(74) *Attorney, Agent, or Firm* — Seed IP Law Group PLLC (57) ABSTRACT

An integrated capacitive-type humidity sensor formed in a semiconductor chip integrating a sensing capacitor and a reference capacitor. Each of the sensing and reference capacitors have at least a first electrode and at least a second electrode, the first and second electrodes of each of the sensing and reference capacitors being arranged at distance and mutually insulated. A hygroscopic layer extends on the sensing and reference capacitors and a conductive shielding region extends on the reference capacitor but not on the sensing capacitor.

20 Claims, 6 Drawing Sheets

(56) References Cited

U.S. PATENT DOCUMENTS

| | | | |
|---|---|---|---|
| 2005/0218465 A1* | 10/2005 | Cummins | 257/414 |
| 2006/0186901 A1* | 8/2006 | Itakura et al. | 324/689 |
| 2006/0260107 A1* | 11/2006 | Itakura et al. | 29/25.03 |
| 2008/0061802 A1* | 3/2008 | Alimi et al. | 324/689 |
| 2008/0257037 A1* | 10/2008 | Isogai et al. | 73/335.04 |
| 2010/0102410 A1* | 4/2010 | Shimizu et al. | 257/435 |
| 2011/0314922 A1* | 12/2011 | Ismail et al. | 73/718 |
| 2012/0304742 A1* | 12/2012 | Cummins | 73/31.06 |
| 2013/0207673 A1* | 8/2013 | Tondokoro | G01N 27/223 324/664 |
| 2014/0139241 A1* | 5/2014 | Sakai | G01N 27/223 324/665 |

\* cited by examiner

INTEGRATED DEVICE OF A CAPACITIVE TYPE FOR DETECTING HUMIDITY, IN PARTICULAR MANUFACTURED USING A CMOS TECHNOLOGY

BACKGROUND

1. Technical Field

The present disclosure relates to an integrated device of a capacitive type for detecting humidity, in particular manufactured using a CMOS technology 2. Description of the Related Art Presently, devices for detecting humidity or hygrometers are widely used for a variety of applications, including controlling humidity of industrial, agricultural, and living environments. In particular, in view of the current trend to miniaturization and the preference for arranging small dimension hygrometers in portable apparatuses, a desire is increasingly felt of having integrated hygrometers of very small dimensions.

Figure 1:
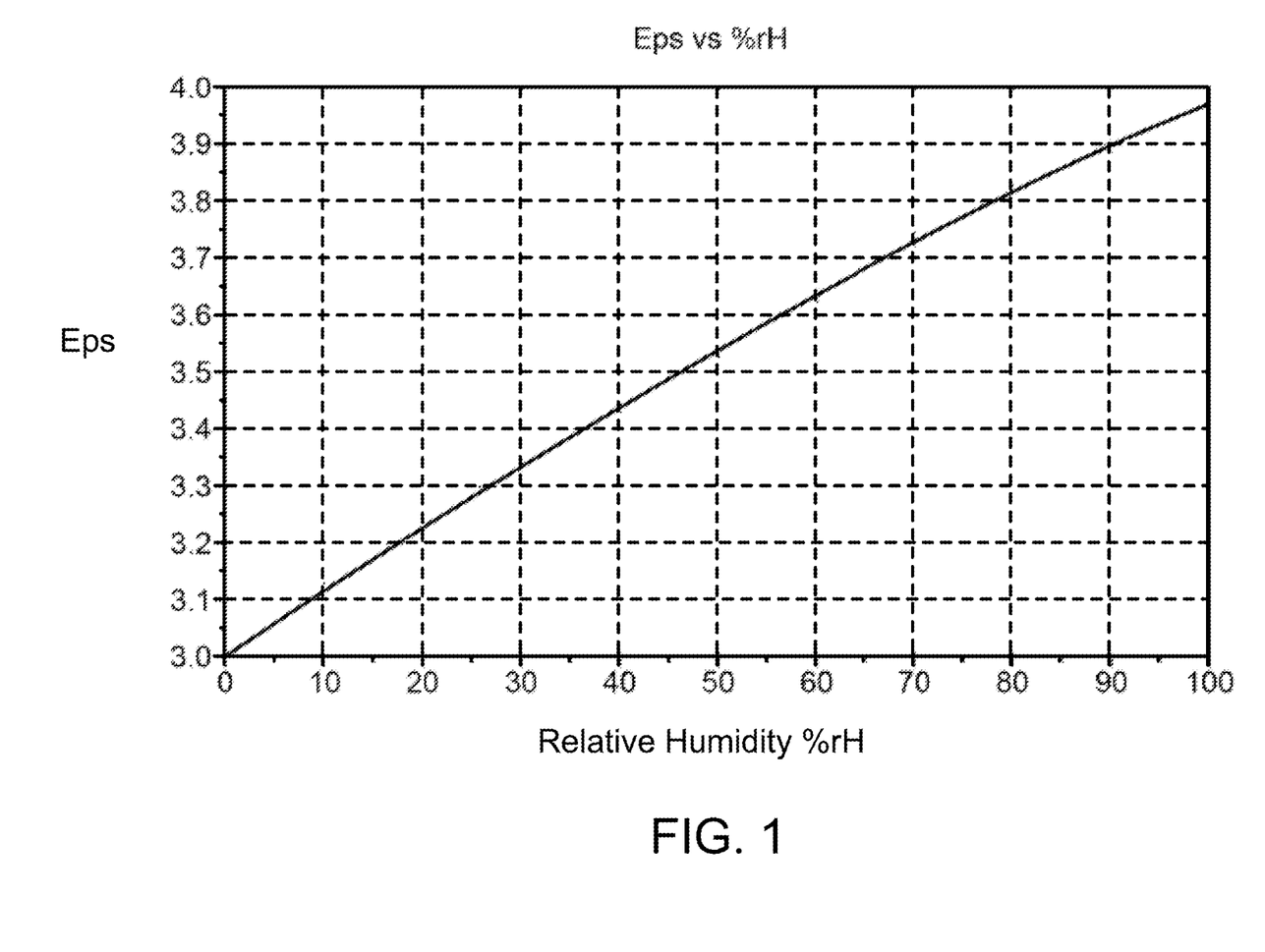
FIG. 1 shows the behavior of the change in the dielectric constant of a polyimide layer versus absorbed humidity.

To this end, integrated hygrometers manufactured using a semiconductor technology have already been proposed, since they have good accuracy, based on exploiting the ability of a hygroscopic material to change an electric property of the device as a function of absorbed water particles. In particular, polyimide layers have been proposed, since they undergo a linear variation of their dielectric constant $\in_{ps}$ as a function of relative humidity, according to the behavior shown in FIG. 1.

Electronic chips forming capacitive-type humidity sensors have been already disclosed (see, e.g., U.S. 2005/0218465 and H. Shimizu, H. Matsumotu et al: "A Digital Hygrometer" IEEE Transactions on Instrumentation and Measurement, Vol. 37, No. 2, June 1988). The known devices include a sensing capacitor formed in a sensing layer on top of a silicon substrate and having metal fingered electrodes. A hygroscopic layer of, e.g., polyimide, covers or overlies the metal fingered electrodes of the sensing capacitor. The top hygroscopic layer is thus able to capture water particles of the external environment and to change its dielectric constant as a function of environmental humidity. Thus, also the capacity of the sensing capacitor varies, and the variation can be read by a suitable circuit, including, e.g., an input capacitive bridge.

Humidity sensors may be formed of the single and differential type.

Both types are however susceptible to improvements. In fact, the single-type humidity sensors typically utilize a small area, but are affected by matching inaccuracies and ageing. On the other hand, the differential-type humidity sensors are less affected by matching and ageing but utilize a much bigger area and are subject to leakage.

In particular, the differential solution may be based on forming a reference capacitor near the sensing capacitor and having the same structure as the sensing capacitor, but for the hygroscopic layer. In one solution, the reference capacitor may have no hygroscopic layer at all; in another solution, the reference capacitor may be shielded from the external environment.

In both cases, the reference capacitor is intended to be insensitive to humidity changes but follow the behavior of the sensing capacitor in all other aspects, so that the variations in the electric characteristics due to ageing, temperature, manufacturing spread and so on are the same, so that a reading circuit is able to detect property changes in the sensing capacitor caused by changes in humidity of the external environment and to distinguish them from other effects.

However, with the increasing miniaturization of the integrated devices, both solutions are not sufficient to ensure the desired insensitivity to humidity.

In fact, in the first case (where the reference capacitor has no hygroscopic layer), the latter has to be removed from the reference capacitor after being deposited on the entire surface of the wafer. However, the absence of the hygroscopic layer on the reference capacitor weakens the structure, because it involves forming an aperture in the layer, thus impairing its function as a mechanical protection and as humidity barrier. In addition, removal is costly and critical, since removal of the hygroscopic material from adjacent, sensing areas is to be avoided and limits the desired miniaturization.

On the other hand, the shielding solution has proven insufficient. Shielding may be obtained by depositing a humidity blocking layer of a different non-hygroscopic dielectric material over or under the hygroscopic layer. However, with this solution, the reference capacitor cannot be made insensitive to external humidity, as also recognized in U.S. 2005/0218465. Similar problem are encountered if the shielding layer is arranged between the electrodes and the hygroscopic material. In fact, with horizontal miniaturization of sensors, electric field lines exiting from an electrode finger and closing in an adjacent, oppositely biased electrode finger have a considerably vertical extension and may reach the hygroscopic layer, so that the reference capacitor is not insensitive to humidity. To avoid this, a very thick shielding layer may be used, with thicknesses of more than ten microns. Such thicknesses cannot be reached with standard machines and deposition techniques, which currently allow deposition of dielectric layers having standard maximum thicknesses of about one micron. Thus, no efficient shielding can be reached with either solution.

BRIEF SUMMARY

One or more embodiments of the present disclosure are directed to an integrated humidity sensor and a process for manufacturing it. For instance, one embodiment is directed to a humidity sensor comprising a semiconductor chip. A sensing capacitor and a reference capacitor are integrated in the semiconductor chip, each of the sensing and reference capacitors having at least a first electrode and at least a second electrode, the first and second electrodes of each of the sensing and reference capacitors being arranged at a distance from each other and mutually insulated. The sensor further includes a hygroscopic layer over the sensing and reference capacitors and a conductive shielding region over the reference capacitor. The conductive shielding region is not located over the sensing capacitor.

BRIEF DESCRIPTION OF THE SEVERAL VIEWS OF THE DRAWINGS

For the understanding of the present disclosure, preferred embodiments are now described, purely as a non-limitative example, with reference to the enclosed drawings, wherein.

DETAILED DESCRIPTION

Figure 2:
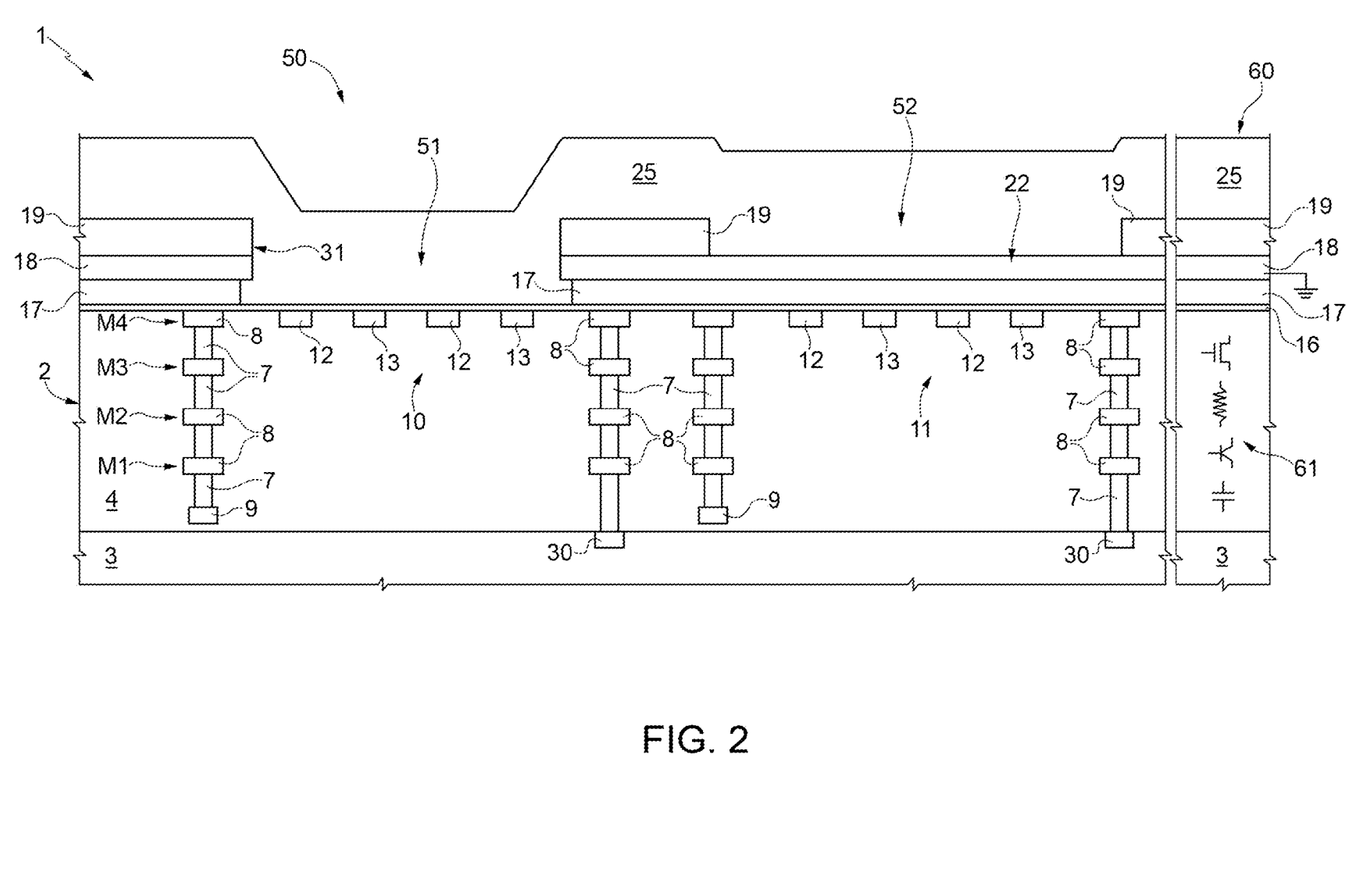
FIG. 2 is a cross-section of an embodiment of the present hygroscopic sensor.

FIG. 2 shows an embodiment of an integrated humidity sensor 1 fabricated using a HCMOS (High speed CMOS) technology, with the sensor 1 formed in a backend manufacturing step.

In detail, the sensor 1 is formed in a chip 2, including a semiconductor substrate 3, e.g., of silicon, and an insulating structure 4, overlying the substrate 3. Specifically, the sensor 1 is formed in a sensing portion 50 of the chip 2. A processing portion 60 may also be provided, laterally to the sensing portion 50, in a per se known manner, to integrate reading and processing circuitry components 61.

In turn, the sensing portion 50 includes a sensing capacitor area 51 and a reference capacitor area 52.

The insulating structure 4 is typically formed by a plurality of superimposed insulating layers, not separately shown, accommodating a plurality of metal regions 8 formed in a plurality of metal levels (here four), indicated by M1 (lower metal level), M2 (first intermediate metal level) and M3 (second intermediate metal level) and M4 (upper metal level) mutually connected through vias 7. The metal regions 8 may be of aluminum. In addition, the metal regions 8 of the lower metal level M1 may be connected to conductive regions 9 on the substrate 3 and/or to conductive regions 30 in the substrate 3.

Figure 3:
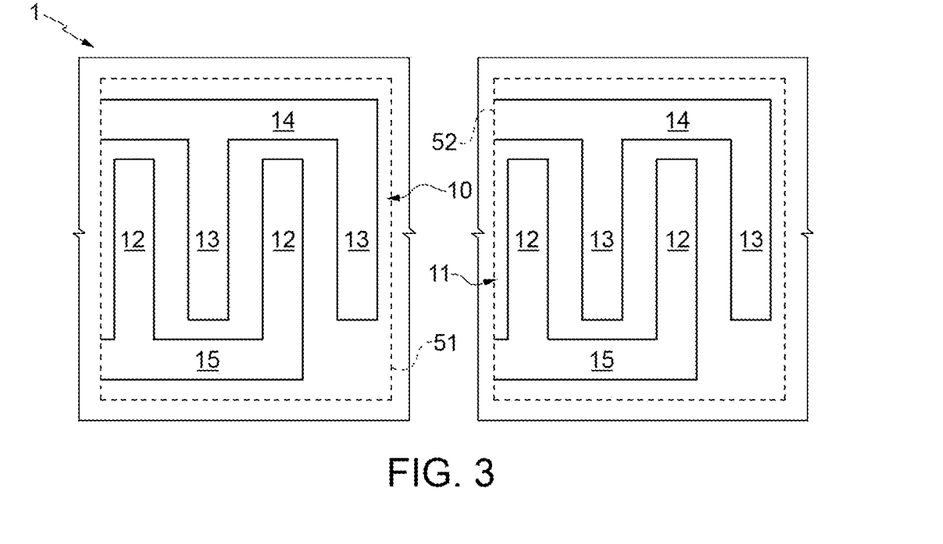
FIG. 3 is a top view of the sensor of FIG. 3.

The metal regions 8 of the upper metal level M4 form, for example, first and second electrodes 12, 13 of a sensing capacitor 10 and of a reference capacitor 11 arranged respectively in the sensing capacitor area 51 and in the reference capacitor area 52. As visible in the top view of FIG. 3, the capacitors 10, 11 are of a multifingered, interdigitated type, with the first electrodes 12 connected together by a conductive line 15 and biased at a first potential (e.g., a higher potential), and the second electrodes 13 connected together by a conductive line 14 and biased at a second potential (e.g., a lower potential).

Referring again to FIG. 2, protection layer 16, e.g., of nitride, extends on the entire upper surface of the insulating structure 4 to protect the electrodes 12, 13 from water molecules of the environment that may cause any oxidation thereof and a dielectric layer 17, e.g., of oxide ("padopen oxide"), extends on the protection layer 16, except for in the sensing capacitor area 51. In particular, the dielectric layer 17 extends in the reference capacitor area 52.

A conductive shielding layer 18 extends on the dielectric layer 17, except for on the sensing capacitor area 51. The conductive shielding layer 18 is of a good electric conductive material, with a resistivity lower than 50 mΩ/□, such as a metal, for example aluminum, that is impervious to water molecules and may have a thickness of about 1 µm. Therefore, in the reference capacitor area 52, the conductive shielding layer 18 forms an electrical shield 22.

A passivation layer 19 of insulating material, for example a double layer of PSG (Phosphorous Silicon Glass) and nitride, extends on the conductive shielding layer 18, except for in the sensing capacitor area 51 and, here, on the reference capacitor area 52.

A hygroscopic layer 25 extends on the entire surface of the sensing portion 50 of chip 1, over the passivation layer 19, where present, and directly on the protection layer 16, in the sensing capacitor area 51, or on the electrical shield 22, in the reference capacitor area 52. The hygroscopic layer 25 is a thick layer, compared with the other layers; for example its thickness may be less than 10 µm. The hygroscopic layer 25 may be the so called "pix", that is an aqueous positive polyimide, which can be defined with high resolution and has storage and room temperature stability that is used in the semiconductor industry, or another polyimide material or another polymeric material. In addition, also porous low-K silicon dioxide may be used.

Figure 4:
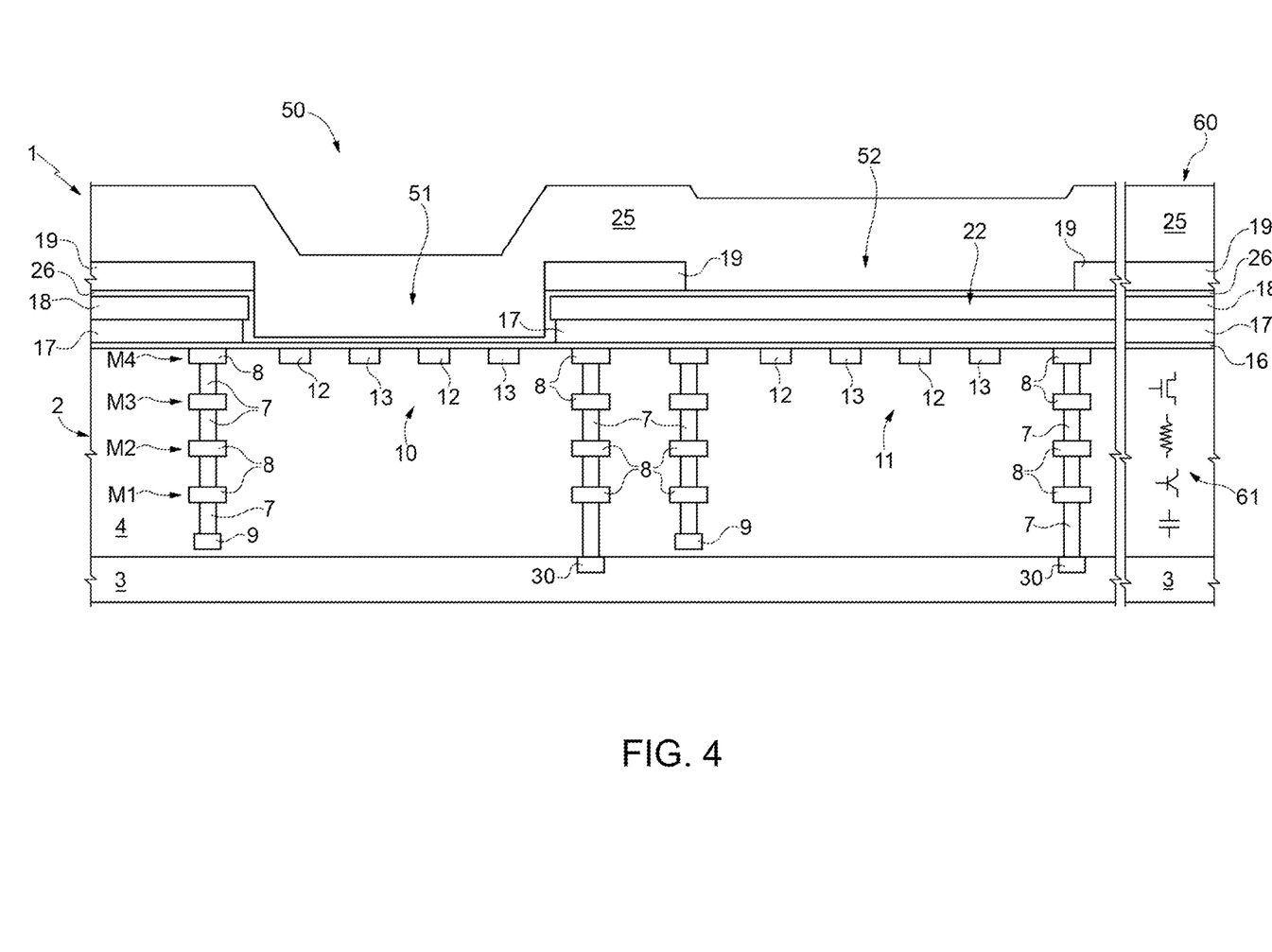
FIG. 4 is a cross-section of another embodiment of the present hygroscopic sensor.

FIG. 4 shows a different embodiment, wherein the shielding layer is covered by a further protection layer 26, e.g., of nitride, acting as a humidity barrier for protecting the electrical shield 22 from any water molecules reaching it. The further protection layer 26 has a thickness lower than 0.5 µm, for example 0.1-0.2 µm, to avoid a loss of sensitivity of the sensing capacitor 10. In the alternative, the further protection layer 26 may be removed from the sensing capacitor area 51.

Figure 5:
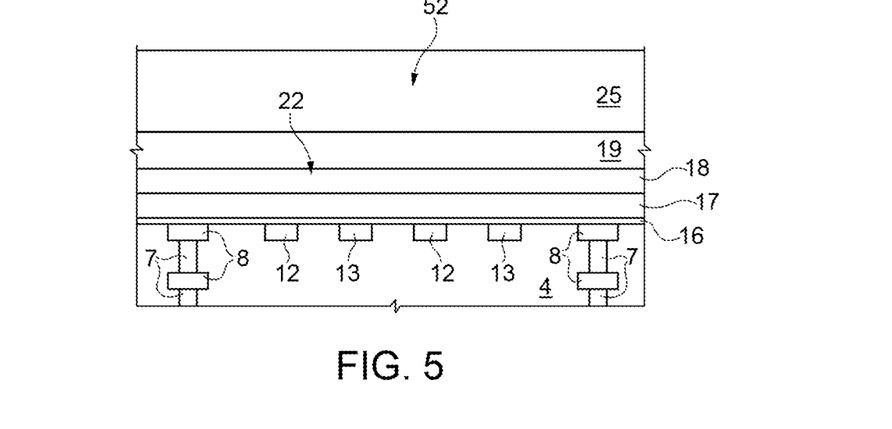
FIG. 5 is a cross-section showing a different detail of the present hygroscopic sensor.

According to another embodiment, the passivation layer 19 is not removed from the reference capacitor area 52, as shown in FIG. 5.

Figure 6:
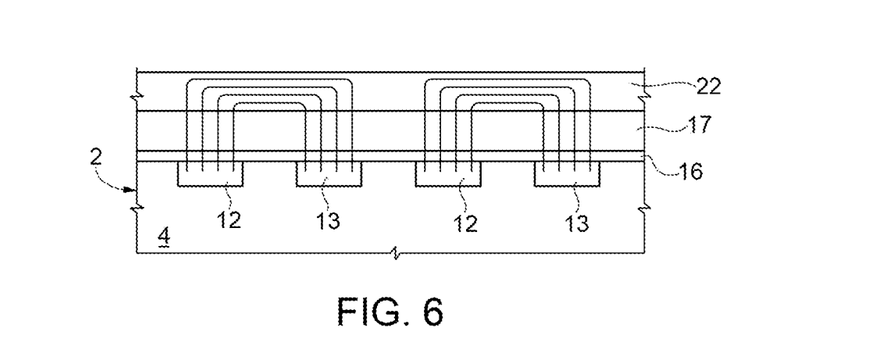
FIG. 6 is an enlarged cross-sectional view showing electric field lines in a portion of the present sensor.

In all the above embodiments, by virtue of the conductive shielding layer 18 that covers the reference capacitor 11, the electric field lines extending between the first and second electrodes 12, 13 are bent and constrained to pass along the conductive shielding layer 18, as shown in the enlarged detail of FIG. 6.

Thereby, the electric field lines cannot reach the hygroscopic layer 25 in the reference capacitor area 52 so that the reference capacitor 11 is insensitive to the humidity content of the hygroscopic layer 25. Thus, the reference capacitor 11 does not change its electric property, in particular its capacity, as a function of the humidity of the external environment.

Figure 7:
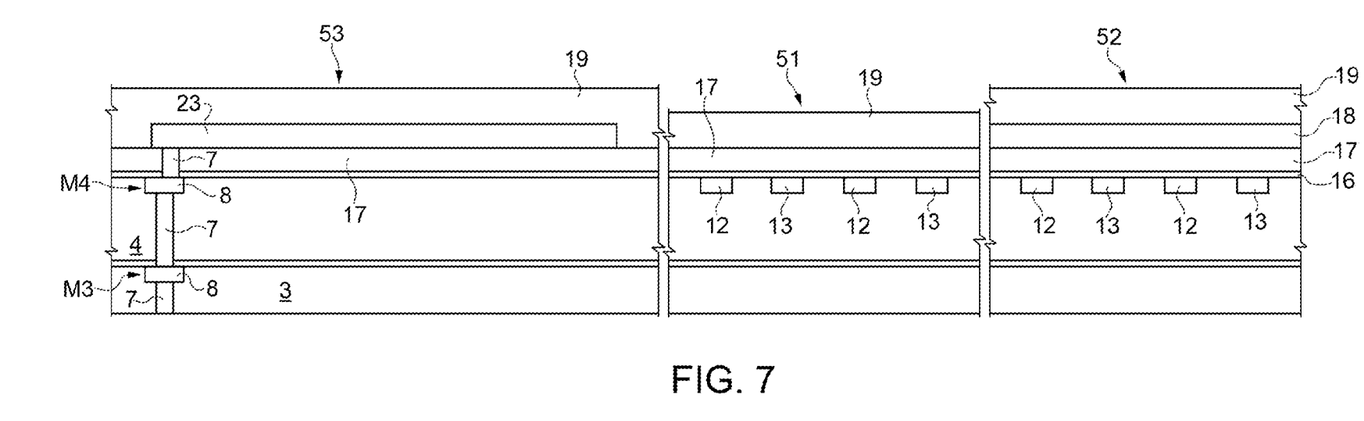
FIGS. 7-9 show cross-sections of the sensor of FIG. 1, in various manufacturing steps.
Figure 8:
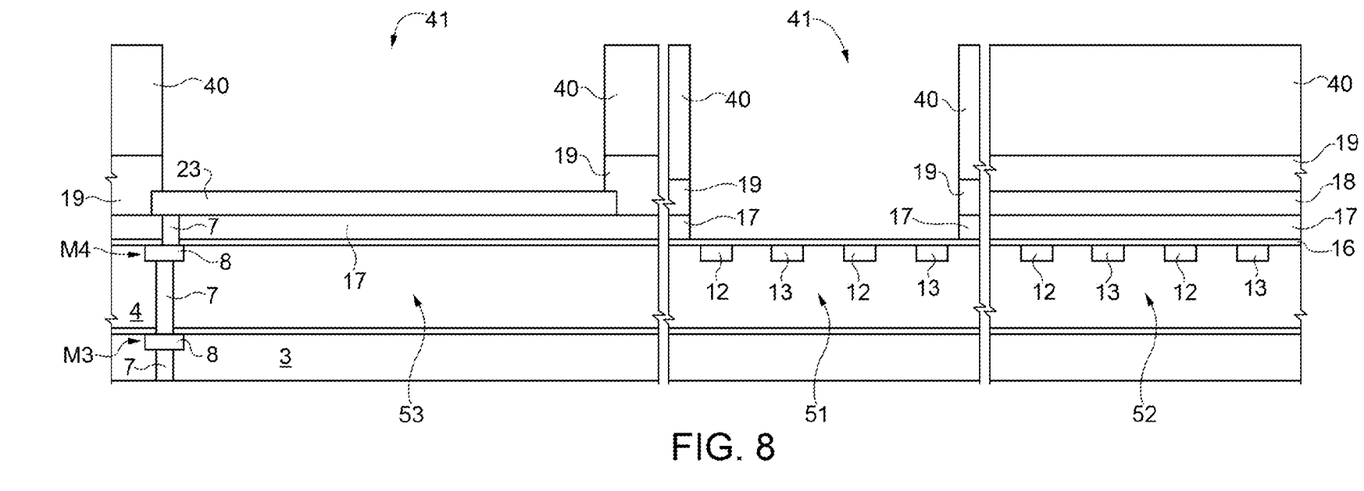
Figure 9:
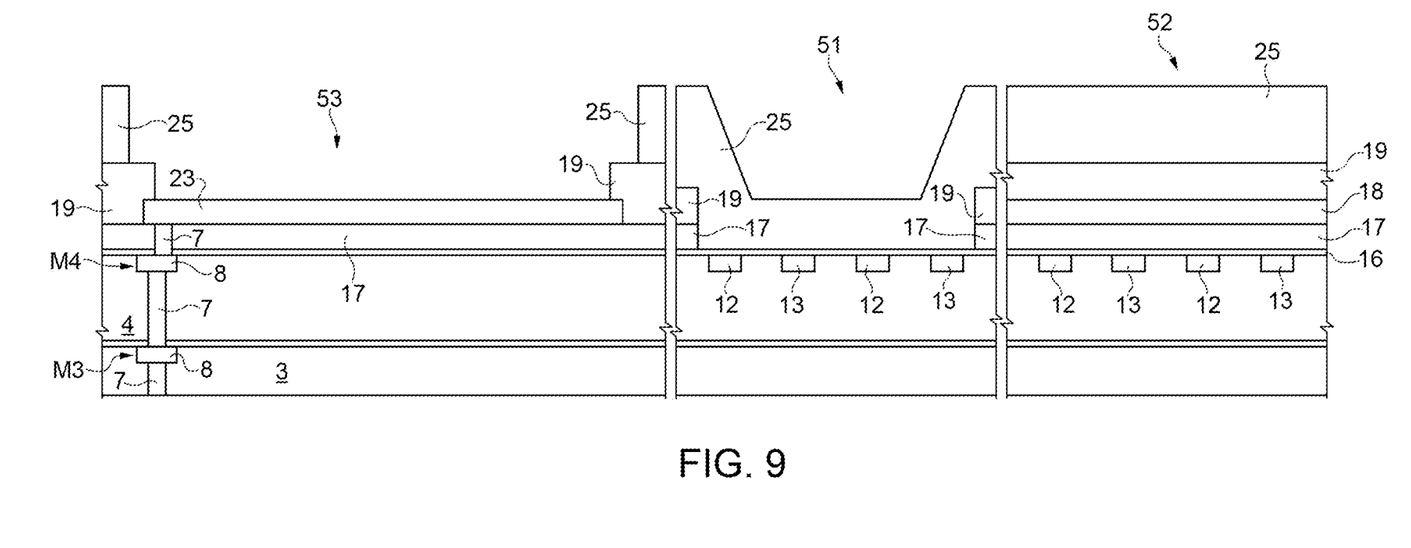

FIGS. 7-9 show subsequent manufacturing steps for the integrated humidity sensor 1. In particular, an upper portion of the chip 2 is shown, including the two upper metal levels M3, M4, the upper portion of the insulating structure 4 and the overlying layers. In particular, FIGS. 7-9 show the sensing capacitor area 51, the reference capacitor area 52 and a pad area 53.

Initially, after forming the integrated electronic components 61 in the substrate 3 (FIG. 2), the insulating structure 4 is formed by depositing alternating silicon nitride and silicon dioxide layers and forming conductive regions 8 of metal and respective vias 7. In particular, when the fourth or upper metal layer M4 is formed, the electrodes 12, 13 and the conductive lines 14, 15 of the sensing and reference capacitors 10, 11 are also formed.

The protection layer 16 and the dielectric layer 17 are deposited; and the conductive shielding layer 18 is formed on the dielectric layer 17. To this end, a metal layer (such as aluminum) is deposited on the entire surface of the dielectric layer 17 and etched away from the sensing capacitor area 51 or selected portions of metal are formed, e.g., grown on the dielectric layer 17. In any case, the conductive shielding layer 18 extends on the reference capacitor area 52, where it forms the electrical shield 22, and on the pad area 53, where it forms pads 23.

Thereafter, the passivation layer 19 is deposited on the entire surface of the chip 2, obtaining the structure of FIG. 7.

As shown in FIG. 8, a resist mask 40 is formed. Here, the resist mask 40 covers the reference capacitor area 52 and has openings or windows 41 over the sensing capacitor area 51 and the pad area 53. Using the resist mask 40, the exposed portion of the passivation layer 19 is etched from the pad area 53; in addition, the exposed portions of the passivation layer 19 and then of the protection layer 16 are removed from the sensing capacitor area 51. Thereby, the structure of FIG. 8 is obtained.

After removing the resist mask 40, FIG. 9, the hygroscopic layer 25 is deposited and removed from the pad area 53. Thereby, the final structure of FIG. 9 is obtained.

According to a different embodiment, during the etching of the passivation layer 17 from the pad area 53 and the sensing capacitor area 51, the passivation layer 17 may also be removed from the reference capacitor area 52.

Figure 10:
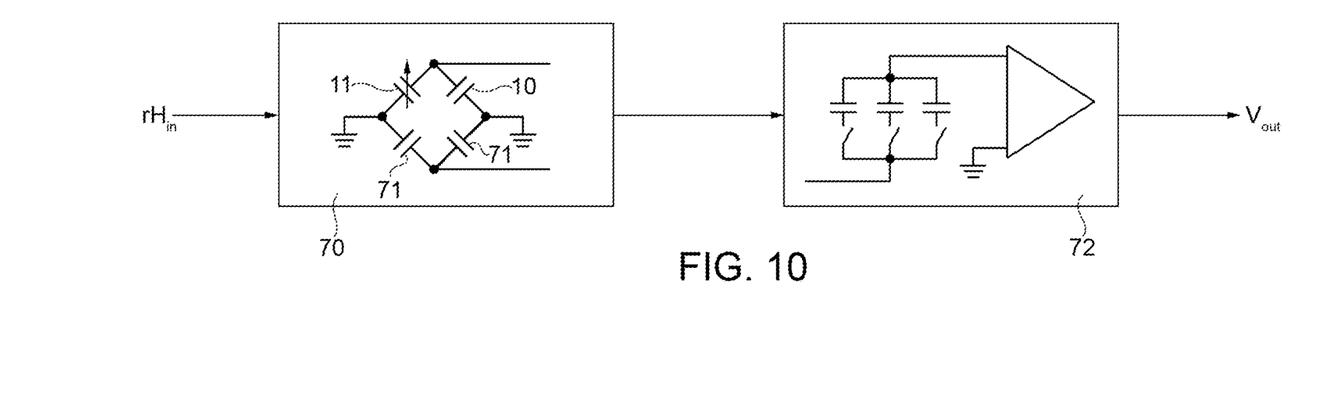
FIG. 10 is a block diagram of a humidity reading device.

The sensor 1 may be integrated together with a processing circuitry, as shown in FIG. 10, where the processing circuitry components 60 (FIG. 2) are integrated in a specific area of the chip 2. In particular, the processing circuitry components 60 may form a bridge 70, together with the sensing capacitor 10, the reference capacitor 11 and standard capacitors 71. The capacity variation of the bridge 70 is then converted into an output voltage signal through for example a switched-capacitor operational amplifier 72 having an input coupled to the bridge 70.

The advantages of the present disclosure are clear from the above. In particular, it is emphasized that the present sensor is able to measure the environmental humidity in a reliable way through a differential technique, due to the reference capacitor 11 that is substantially unaffected by moisture, even at high levels of the latter.

The sensing and the reference capacitors are matched so that the thermal behavior and the ageing effect may be compensated in a differential reading; thereby the humidity sensor is unaffected by variations in environmental condition (except humidity) or over time.

The sensor may be manufactured in a simple and economic way, since no critical patterning operations are needed for the hygroscopic material. If a polyimide layer is used, the manufacture is quite simple and economic, since this material is routinely used as a mechanical environmental protection in standard silicon CMOS processes.

The humidity sensor disclosed therein may be used in weather stations; HVACs (Heating, Ventilation and Air Conditioning systems); respiratory equipment; humidifiers; gas sensors measurement correction; condensation level monitoring; air density monitoring; multiple type interfaces.

Finally, it is clear that numerous variations and modifications may be made to the humidity sensor described and illustrated herein.

For example, the conductive shielding layer 18 may be of a different conductive material that has high conductivity (typically, a resistivity lower than 50 mΩ/□) and is substantially impervious to water molecules. Moreover, the conductive shielding region 22 may be arranged over the hygroscopic layer 25. In addition, if the hygroscopic layer 25 ha as sufficient thickness to avoid the captured molecules to reach the electrodes 12, 13, the protection layer 16 may be omitted.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A humidity sensor, comprising:
   a semiconductor chip;
   a sensing capacitor and a reference capacitor integrated in the semiconductor chip, each of the sensing and reference capacitors having a first electrode and a second electrode, the first and second electrodes of each of the sensing and reference capacitors being arranged at a distance from each other and mutually insulated;
   a hygroscopic layer over the sensing and reference capacitors; and
   a conductive shielding region over the reference capacitor and between the hygroscopic layer and the reference capacitor and not over the sensing capacitor.

2. The sensor according to claim 1, wherein the hygroscopic layer is located over the conductive shielding region in a reference capacitor area of the chip that includes the reference capacitor.

3. The sensor according to claim 1, wherein the semiconductor chip comprises an insulating structure that includes a plurality of metal regions arranged in a plurality of metal levels, the first and second electrodes of the sensing and reference capacitors being formed by respective metal regions.

4. The sensor according to claim 3, wherein the plurality of metal levels includes an upper metal level, the first and second electrodes of the sensing and reference capacitors are formed in the upper metal level.

5. A semiconductor chip;
   a sensing capacitor and a reference capacitor integrated in the semiconductor chip, each of the sensing and reference capacitors having a first electrode and a second electrode, the first and second electrodes of each of the sensing and reference capacitors being arranged at a distance from each other and mutually insulated;
   a hygroscopic layer over the sensing and reference capacitors;
   a conductive shielding layer over the reference capacitor and not over the sensing capacitor;
   an insulating structure that includes a plurality of metal regions arranged in a plurality of metal levels, the first and second electrodes of the sensing and reference capacitors being formed by respective metal regions; and
   a passivation layer over the conductive shielding layer, the conductive shielding layer and passivation layer having an opening over the sensing capacitor.

6. The sensor according to claim 3, wherein the sensing and reference capacitors each comprise a plurality of first and second electrodes, the first electrodes of the sensing capacitor being coupled together by a first line, the second electrodes of the sensing capacitor being coupled together by a second line, the first electrodes of the reference capacitor being coupled together by a third line, the second electrodes of the reference capacitor being coupled together by a fourth line, and the first electrodes and second electrodes of the respective sensing and reference capacitors being interdigitated.

7. The sensor according to claim 1, wherein the first and second electrodes of the sensing and reference capacitors have the same structure and shape as each other, and the sensing and reference capacitors extend laterally and at a distance to each other.

8. The sensor according to claim 1, wherein the hygroscopic layer is one of a polymeric material and a low-K dielectric material.

9. The sensor according to claim 8 wherein the hygroscopic layer is polyimide.

10. The sensor according to claim 1, comprising:
    a capacitor bridge including the sensing and reference capacitors;

an operational amplifier having an input coupled to the capacitor bridge; and an output generating an output signal indicative of humidity.

11. An apparatus comprising:

a humidity sensor that includes:
- a semiconductor chip;
- a sensing capacitor and a reference capacitor in the semiconductor chip, each of the sensing and reference capacitors having first electrodes and second electrodes, the first and second electrodes of each of the sensing and reference capacitors being arranged at a distance from each other;
- a hygroscopic layer over the sensing and reference capacitors;
- a conductive shielding region over the reference capacitor, the conductive shielding region not being over the sensing capacitor; and
- a dielectric layer over the conductive shielding region but not over the sensing capacitor.

12. The apparatus according to claim 11, wherein the apparatus is one of a weather station, a HVAC, a respiratory equipment, a humidifier, a gas sensor, a condensation level monitoring apparatus, and an air density monitoring apparatus.

13. The apparatus according to claim 11, wherein the hygroscopic layer is a polymeric material.

14. The apparatus according to claim 11, wherein the hygroscopic layer is located over the conductive shielding region in a reference capacitor area of the chip that includes the reference capacitor.

15. A process for manufacturing a humidity sensor, the process comprising:

forming a sensing capacitor and a reference capacitor in a semiconductor body, wherein forming the sensing and the reference capacitors comprises forming, for each of the sensing and reference capacitors, a first electrode and a second electrode, the first and second electrodes being arranged at a distance from each other and mutually insulated;

forming a hygroscopic layer on the sensing and reference capacitors, wherein forming a conductive shielding region comprises:
- forming, on the insulating structure, a conductive shielding layer;
- forming a passivation layer on the conductive shielding layer; and
- removing the passivation layer and the conductive shielding layer from above the sensing capacitor; and forming a conductive shielding region on the reference capacitor and not forming the conductive shielding region on the sensing capacitor.

16. The process according to claim 15, wherein forming the sensing capacitor and the reference capacitor comprises:

forming an insulating structure; and forming a plurality of metal regions arranged in a plurality of metal levels that includes an upper metal layer, wherein the first and second electrodes of the sensing and reference capacitors are formed by respective metal regions in the upper metal layer.

17. The process according to claim 15, further comprising:

patterning the conductive shielding layer to form the conductive shielding region on the reference capacitor and at least one pad in a pad area of the body;

removing the passivation layer over the least one pad; and removing the hygroscopic layer from the pad area.

18. The sensor according to claim 5, wherein the first and second electrodes of the sensing and reference capacitors have the same structure and shape as each other, and the sensing and reference capacitors extend laterally and at a distance to each other.

19. The sensor according to claim 5, wherein the hygroscopic layer is one of a polymeric material and a low-K dielectric material.

20. The sensor according to claim 5, comprising:
- a capacitor bridge including the sensing and reference capacitors;
- an operational amplifier having an input coupled to the capacitor bridge; and
- an output generating an output signal indicative of humidity.

* * * * *